United States Patent [19]

Weferling

[11] Patent Number: 4,536,350
[45] Date of Patent: Aug. 20, 1985

[54] PROCESS FOR MAKING CHLOROPHOSPHANES, PHOSPHINIC ACID CHLORIDES OR THIOPHOSPHINIC ACID CHLORIDE, AND NOVEL ISOMERIC MIXTURE CONSISTING OF CHLORO-PHOSPHABICYCLONONANES

[75] Inventor: Norbert Weferling, Frechen, Fed. Rep. of Germany

[73] Assignee: Hoechst Aktiengesellschaft, Fed. Rep. of Germany

[21] Appl. No.: 532,273

[22] Filed: Sep. 14, 1983

[30] Foreign Application Priority Data

Sep. 28, 1982 [DE] Fed. Rep. of Germany ....... 3235787

[51] Int. Cl.$^3$ .............................. C07F 9/52; C07F 9/53
[52] U.S. Cl. ................................................. 260/543 P
[58] Field of Search ..................................... 260/543 P

[56] References Cited

U.S. PATENT DOCUMENTS 3,086,047 4/1963 Hofmann ......................... 260/543 P
3,734,958 5/1973 Rio ................................... 260/543 P

OTHER PUBLICATIONS

Kosolapoff, G. M. et al., *Organic Phosphorus Compounds*, vol. 1, Wiley-Interscience, Publ., (1972), pp. 11, 15, 26 and 38.
Appel, R. et al., *Chemische Berichte*, vol. 110, (1977), p. 23824.

*Primary Examiner*—Natalie Trousof
*Assistant Examiner*—L. Hendriksen
*Attorney, Agent, or Firm*—Connolly and Hutz

[57] ABSTRACT

The disclosure relates to a process for making chlorophosphanes from primary or secondary phosphanes, or phosphinic acid chlorides or thiophosphinic acid chlorides from secondary phosphane oxides or sulfides, wherein the respective starting materials are reacted with hexachloroethane at temperatures of 20° to 180° C. The disclosure also provides as a novel chemical substance an isomeric mixture consisting of 9-Cl-9-phosphabicyclononane [3.3.1] and 9-Cl-9-phosphabicyclononane [4.2.1].

7 Claims, No Drawings

PROCESS FOR MAKING CHLOROPHOSPHANES, PHOSPHINIC ACID CHLORIDES OR THIOPHOSPHINIC ACID CHLORIDE, AND NOVEL ISOMERIC MIXTURE CONSISTING OF CHLORO-PHOSPHABICYCLONONANES

The present invention relates to a process for making chlorophosphanes of the general formula

from primary or secondary phosphanes of the general formula

or phosphinic acid chlorides or thiophosphonic acid chlorides of the general formula

from secondry phoshane oxides or sulfides of the general formula

in which formulae $R^1$ stands for a linear or branched alkyl group, a substituted or unsubstituted aryl or cycloalkyl group having from 1 to 16 carbon atoms, preferably 1 to 8 carbon atoms, $R^2$ has one of the meanings given for $R^1$ or stands for hydrogen, $R^1$ and $R^2$ are —CH-bridge members of a bicyclic ring system consisting of 4 to 6 carbon atoms, $R^3$ has one of the meanings given for $R^1$, X stands for $R^1$ or chlorine, and Y stands for sulfur or oxygen.

The invention also relates to a novel chemical substance which is an isomeric mixture consisting of 9-Cl-9-phosphabicyclononane [3.3.1] and 9-Cl-9-phosphabicyclononane [4.2.1].

Attempts have already been made to produce primary and secondary phosphane halides with the use of chlorine by subjecting organic phosphanes which have two replaceable hydrogen atoms and are directly linked to trivalent phosphorus (cf. U.S. Pat. Nos. 2,437,796 and 2,437,798) to a chlorination reaction.

As the results of these tests were not reproducible, preference has been given to the use of phosgene as a chlorinating agent (cf. E. Steiniger, Chem. Ber. 96, 3184 [1963] and U.S. Pat. No. 3,074,994 and British Specification GB-PS 904 086).

Adverse effects which are associated with this method reside in the hazardous use of very toxic phosgene and in the frequently unsatisfactory yields.

It has now unexpectedly been found that these adverse effects can be obviated in the process of this invention by reacting the starting materials with hexachloroethane at a temperature of 20° to 180° C., preferably 80° to 120° C. It is more particularly advantageous to effect the reaction in the presence of a solvent which should conveniently be selected from linear or branched aliphatic hydrocarbons having more than 5 carbon atoms, methylcyclohexane or aromatic hydrocarbons, such as benzene, toluene or xylenes. The present process avoids operation with toxic phosgene. In addition to this, the chlorination effected with hexachloroethane could not be found to involve further oxidation of the resulting chlorophosphanes to give phosphonium compounds of the type $[R^1R^3P+Cl_2]Cl^-$ and $[R^1P+Cl_3]Cl^-$, respectively.

Under the conditions selected in accordance with this invention, it is possible to produce primary and secondary chlorophosphanes and also phosphinic acid or thiophosphinic acid chlorides from secondary phosphane oxides (phosphane sufides). As compared with the processes used heretofore, wherein secondary phosphane oxides are chlorinated with $PCl_5$ or $SOCl_2$ or secondary phosphane sulfide are reacted with $CCl_4$ in the presence of triethylamine, the present invention provides an alternative chlorination route.

The present process also permits the novel isomeric mixture referred to hereinabove which is a suitable intermediate used in making pharmaceutical preparations and pesticides to be very reliably produced.

The melting point of this mixture of isomeric 9-Cl-9-phosphabicyclononane [3.3.1] and 9-Cl-9-phosphabicyclononane [4.2.1] is 92°–96° C. and the boiling point is 120°–125° C. at $10^{-2}$ mm Hg.

The following examples illustrate the process of this invention which is naturally not limited thereto.

EXAMPLE 1

Preparation of dicyclohexylchlorophosphane 19.8 g (0.1 mol) dicyclohexylphosphane was added dropwise at room temperature to 26.1 g (0.11 mol) hexachloroethane. After the exothermal reaction which took place with evolution of HCl was terminated, the reaction mixture was stirred for 3 hours at 100° C. The yields ($^{31}$-P-NMR) were as follows: δ P=125.2 (($C_6H_{11}$)$_2$PCl, 94 wgt %); δ P=194.4 ($C_6H_{11}$PCl$_2$, 2 wgt %); δ P=76.7 (($C_6H_{11}$)$_2$P(O)Cl, 4 wgt %). The crude product was distilled and 13.7 g (59 wgt %) dicyclohexylchlorophosphane (bp.: 136°–138° C./4 millibars) was obtained.

EXAMPLE 2

Preparation of monocyclohexyldichlorophosphane 250 g (1.05 mol) $C_2Cl_6$ was dissolved in 100 ml toluene while heating to 120° C. Next, 58 g (0.5 mol) $C_6H_{11}PH_2$ was added dropwise, the temperature of the reaction mixture being maintained at 120°–130° C. The whole was allowed to undergo post-reaction over 2 hours, low boilers were removed at room temperature under vacuum and the residue was distilled under vacuum (δP=195; $C_6H_{11}$PCl$_2$, 96 wgt%). The yield was 69.8 g (75 wgt %), bp=41°–42° C. under a pressure of less than 1 millibar.

EXAMPLE 3

Preparation of dicyclohexylphosphonic acid chloride

A solution of 53 g (0.25 mol) dicyclohexylphosphane oxide in 150 ml toluene was added dropwise within 3 hours to a solution of 60 g (0.25 mol) $C_2Cl_6$ in 60 ml toluene. The temperature of the reaction mixture was at 120°–130° C. 1 hour after gas ceased to be evolved, all volatile matter was removed at 50° C. under vacuum and the residue was recrystallized from hot benzene.

Yield: 18.7 g=30 wgt %; bp: 105° C., δ P=79.7 ($C_6D_6$). Analysis: calculated P=12.5 wgt %, found P=12.5 wgt %.

EXAMPLE 4

Preparation of dicyclohexylthiophosphinic acid chloride

A mixture of 46.4 g dicycyclohexylphosphane sulfide and 47.4 g hexachloroethane was heated for 6 hours to 140° C. Formed tetrachloroethane was removed under vacuum and 51 g (96 wgt %) crude product (($C_6H_{11}$)$_2$P(:S)Cl, δ P=119.1, 99 wgt %) was retained. It was recrystallized from toluene. Yield: 43 g=81 wgt %, melting point=89°–90° C.

Examples 5 to 9 are summarized in the following Table:

TABLE

| Ex. | Compound reacted with hexachloroethane | Reaction product | React temp. °C. | Solvent | Reaction Period (h) | Yield ($^{31}$P-NMR | |
|---|---|---|---|---|---|---|---|
| 5 | 9-H—phosphabicyclononane isomer mixture (3.3.1) and (4.2.1) | 9-Cl—phosphabi-cyclononane, isomer mixture | 95–120 | toluene | 3 | δP = 134<br>δP = 88 | } 99 wgt % |
| 6 | t-butylphosphane | t-butyldichloro- | 60–120 | toluene | 5 | δP = 199, | 48 wgt % |
| 7 | dioctylphosphane | dioctylchloro-phosphane | 100 | toluene | 4 | δP = 112, | 82 wgt % |
| 8 | phenylphosphane | phenyldichloro-phosphane | 150 | — | 5 | δP = 161, | 74 wgt % |
| 9 | di-n-octylphosphine oxide | di-n-octylchloro-phosphinic acid | 90–120 | toluene | 4 | δP = 54, | 70 wgt % |

We claim:

1. A process for making chlorophosphanes of the general formula

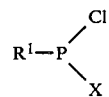

(I)

from primary or secondary phosphanes of the general formula

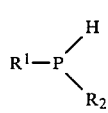

(II)

or phosphinic acid chlorides of thiophosphinic acid chlorides of the general formula

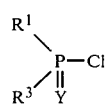

(III)

from secondary phosphane oxides or sulfides of the general formula

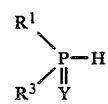

(IV)

in which formulae $R^1$ stands for a linear or branched alkyl group, an aryl or cycloalkyl group having from 1 to 16 carbon atoms, $R^2$ has one of the meanings given for $R^1$ or stands for hydrogen, $R^1$ and $R^2$ are CH-bridge members of a bicyclic ring system which includes the P atom, the two said CH-bridge members, and an additional 4 to 6 carbon atoms, $R^3$ has one of the meanings given for $R^1$, X stands for $R^1$ or chlorine, and X can be $R^2$ when $R^2$ is not hydrogen, and Y stands for sulfur or oxygen, which comprises reacting the respective starting materials with hexachloroethane at temperatures of 20° to 180° C.

2. The process as claimed in claim 1, wherein the reaction is carried out at temperatures of 80° to 120° C.

3. The process as claimed in claim 1, wherein the reaction is carried out in the presence of a solvent.

4. The process as claimed in claim 3, wherein a linear or branched aliphatic hydrocarbon having more than 5 carbon atoms, methylcyclohexane or an aromatic hydrocarbon is used as the solvent.

5. The process as claimed in claim 4, wherein benzene, toluene or a xylene is used.

6. A process as claimed in claim 1, wherein the resulting chlorophosphane has the formula

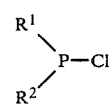

(I)

and is obtained from a secondary phosphanes of the formula

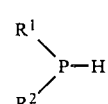

(II)

wherein $R^1$ and $R^2$ are CH-bridge members of a phosphabicyclononane.

7. A process as claimed in claim 1, wherein the resulting chlorophosphane has the formula

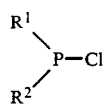

and is obtained from a secondary phosphane of the formula

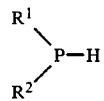

wherein $R^1$ and $R^2$ are

bridge members of a bicyclic ring system of the type $$\begin{array}{c} H \\ | \\ C \\ (CH_2)_m \diagup \quad \diagdown (CH_2)_n \\ \diagdown \quad \diagup \\ C \\ | \\ H \end{array}$$

wherein $m=n=3$ or $m=2$ and $n=4$.

* * * * *